US008475530B2

(12) United States Patent
Pizzoli et al.

(10) Patent No.: US 8,475,530 B2

(45) Date of Patent: Jul. 2, 2013

(54) MIDDLE EAR DIRECT ACTION IMPROVED HEARING AID AND RELATED INSTALLATION METHOD

(75) Inventors: Lamberto Pizzoli, Rome (IT); Nino Camillo Rosica, Rome (IT)

(73) Assignee: Med-El Elektromedizinische Geraete GmbH, Innbruck (AT)

( * ) Notice: Subject to any disclaimer, the term of this patent is extended or adjusted under 35 U.S.C. 154(b) by 90 days.

(21) Appl. No.: 13/105,214

(22) Filed: May 11, 2011

(65) Prior Publication Data

US 2011/0213196 A1 Sep. 1, 2011

Related U.S. Application Data

(63) Continuation of application No. 12/376,369, filed as application No. PCT/IT2007/000532 on Jul. 26, 2007, now abandoned.

(51) Int. Cl.
*A61F 2/18* (2006.01)

(52) U.S. Cl.
USPC .............................................. 623/10; 600/25

(58) Field of Classification Search
USPC .............................................. 623/10; 600/25
See application file for complete search history.

(56) References Cited

U.S. PATENT DOCUMENTS 3,751,605 A * 8/1973 Michelson ..................... 623/10

FOREIGN PATENT DOCUMENTS

EP 1035753 * 9/2000

* cited by examiner

*Primary Examiner* — David Isabella
*Assistant Examiner* — Suba Ganesan
(74) *Attorney, Agent, or Firm* — Sunstein Kann Murphy & Timbers LLP

(57) ABSTRACT

A middle ear prosthesis device and corresponding implantation procedure are described. A sensing microphone converts an acoustic audio signal into a corresponding electrical audio signal. A sensing amplifier amplifies the electrical audio signal. An audio transducer converts the amplified electrical audio signal into a corresponding amplified acoustic audio signal. An acoustic waveguide conducts the amplified acoustic audio signal from the audio transducer to the middle ear and includes: i. a main tubular portion having an outer end for placement in the outer ear canal and an inner end for placement in the middle ear, and ii. an extension portion having an outer end coupleable to the audio transducer and an inner end coupleable to the outer end of the main tubular portion.

4 Claims, 8 Drawing Sheets

MIDDLE EAR DIRECT ACTION IMPROVED HEARING AID AND RELATED INSTALLATION METHOD

This application is a continuation of U.S. patent application Ser. No. 12/376,369, filed Apr. 1, 2009, which is a 35 U.S.C. §371 national phase entry application of Patent Cooperation Treaty Application PCT/IT2007/000532, filed Jul. 26, 2007, which in turn claims priority from Italian Patent Application No. RM2006A000433 filed on Aug. 7, 2006; which are incorporated herein by reference.

TECHNICAL FIELD

This invention relates to an improved acoustic prosthesis having a direct action on the middle ear and a corresponding implantation procedure. More specifically the invention relates to an acoustic prosthesis having a direct action on the middle ear bypassing the tympanic membrane and the ossicles (malleus, incus and stapes) offering great convenience in use for the patient in whom it has been implanted, together with a good level of hygiene.

BACKGROUND ART

It is known that the auditory apparatus may be affected by a variety of malfunctions. Where there is diminished sensitivity we have cases of perceptive hypacusis, while when the middle ear is damaged, either for congenital reasons or as a consequence of chronic infections or trauma, or as a result of surgical causes, such as surgery for radical or modified radical mastoidectomy, we then refer to transmissive and/or mixed hypacusis.

Many acoustic prostheses are currently available to overcome the abovementioned conditions. Among these mention may be made of those which have a direct action on the middle ear. These prostheses having a direct action on the middle ear generally comprise a microphone, possibly means for processing the auditory signal, a loudspeaker or acoustic transducer and a waveguide capable of directly reaching the oval window, bypassing the tympanic membrane and ossicles. In these acoustic prostheses the electronic units (microphone, possible signal processing means, loudspeaker or acoustic transducer) are placed in the auditory canal and are connected to powering batteries by electrical wires.

These types of acoustic prostheses give rise to various problems for users when they have to be removed, if only temporarily. Users in fact often have to be able to remove the prosthesis from their ear, for example for some sports activities such as swimming.

Acoustic prostheses also have to be removed for medical reasons. In fact it is known that metal objects cannot be worn when examinations such as CAT (computerized axial tomography) of the brain or magnetic resonance are performed. Thus, it is desirable that the prosthesis in question should be capable of being easily removed, by another person such as a doctor or nurse or the patient himself, so that the patient can undergo urgent diagnostic procedures.

At the present time some phenomena which have been revealed by investigations into the neurophysiopathology of auditory prostheses, such as:

- secondary adaptability, acclimatization;
- deprivation effects described by various researchers are becoming increasingly important.

It is known that the central nervous system (CNS) must rehabituate itself to the reintroduction of sounds which have disappeared or become attenuated, when they are restored to the auditory circuit following amplification by the prosthesis. In cases of perceptive deafness there is a reduction in the auditory input from the periphery to the central nervous system and either adaptation, which follows a period of acclimatization, or a negative reaction may take place.

As for all the various areas of the human body, including the acoustic areas, there are maps in the cerebral cortex which correspond to neurons originating from the zone of the basal membrane (Corti's organ). Low frequencies are located at the apex of the cochlea and high frequencies at the base.

In the case of unilateral perceptive hypacusis to high frequencies there is a change in the cells of Corti's organ, a thinning or degeneration of the myelin of the nervous fibers, while other cells or fibers remain intact.

Thus, with the passage of time, owing to the lack of stimuli from the periphery to the center, changes take place in the central nervous system corresponding to the areas of projection.

The reduction or absence of inhibiting inputs which should reduce the spontaneous activity of cells in the central nervous system gives rise to significant changes in the central nervous system itself. It is thus understandable that reintroduced amplified sounds can find themselves in an environment which is often greatly changed as a result of anatomical and physiological changes such as for example:

- thinning of the myelin of neurons and synapses, and/or
- changes in spontaneous activity and inhibition.

The introduction of amplified sounds thus gives rise to an appreciable reaction in a system which had already adapted itself to a previous situation, even though a pathological one, and therefore the period of re-adaptation can last for a variably long time.

To sum up, with an acoustic prosthesis there is brought about reorganization of the map of auditory frequencies, "reusing" neurons which no longer respond to the stimuli applied to a damaged cochlear region. This therefore contributes to the hearing of some frequencies which can still be heard. Thus, if frequencies which are no longer heard are now restored through the acoustic prosthesis, competition for their old neurons is set up, thus giving rise to an imbalance in the codification of the sound maps.

The phenomenon of reversibility thus becomes a very important factor. If, however, secondary re-adaptability cannot be brought about with the prosthesis, it is generally better not to keep trying.

The above shows how much more difficult it can be for the adaptability brought about by a prosthesis in a patient with reduced bilateral perceptive hypacusis, when an effort is made to rehabilitate the maps of debilitated high frequency neurons while at the same time also acting on low frequency neurons that are still perfectly functional.

After careful clinical investigations into patients in whom prostheses according to the known art have been implanted, in particular the prosthesis described in patent IT 1294267, of which the Applicants are the proprietor, in which the prosthesis provided for an amplifier located within the auditory canal together with the microphone, these phenomena of secondary adaptability and acclimatization were still present, even though minimally, in 25% to 27% of patients treated.

Thus it was established that in order to overcome the limitations of the prostheses according to the known art it was preferable to reduce occupation of the canal as much as possible, while at the same time maintaining as direct an action as possible on the middle ear.

A further technical problem with acoustic prostheses according to the known art is that of anchoring the extremity of the waveguide. Securing this component makes it possible to stabilize the action of conveying sound to the nerve cells of the middle ear, improving the user's response to the phenomena of secondary adaptability and acclimatization.

At the present time metal hooks attached to the malleus are used to anchor the waveguide. This solution presents various problems. In fact these hooks:

are difficult to attach securely to the extremity of the waveguide located within the middle ear;

can become detached;

are made of metal, which means that the patient will not be able to undergo instrumental examinations such as cranial CAT or magnetic resonance for the reasons mentioned above; and damage the malleus in the long term.

SUMMARY

In the light of the above it is therefore the main object of this invention to provide a prosthesis which leaves the auditory canal substantially free so as to improve the user's adaptability to the prosthesis. Another object of the invention is that of providing an acoustic prosthesis which makes it possible to remove the amplifier from the canal and implant it outside, in contact with the battery, thus also eliminating the Larssen phenomenon ("whistling" from the prosthesis). Another object of the invention is to provide efficient anchorage for the waveguides of these acoustic prostheses within the middle ear.

A specific object of this invention is therefore an improved acoustic prosthesis having a direct action on the middle ear comprising a waveguide of tubular shape, capable of channeling acoustic waves; at least one microphone capable of capturing surrounding sounds; an amplifier electrically connected to the said microphone to amplify the sounds captured by it to a suitable level; at least one audio transducer connected to the said amplifier and the said waveguide, the said transducer converting the electrical signals from the said amplifier into acoustic waves, the said acoustic waves being conveyed through the said waveguide; and means for powering the said amplifier and the said microphone; the said acoustic prosthesis being characterized in that the said waveguide comprises a main portion in which one extremity can be attached within the middle ear while the other extremity can be placed within the auditory canal; and at least one further portion which can be connected to the extremity of the said main portion and the said at least one audio transducer.

Always according to the invention, this prosthesis may comprise a hook member of plastics material, comprising a rigid longitudinal portion and a ring fixed to one extremity of the said rigid longitudinal portion, the said rigid longitudinal portion being capable of being attached close to the said extremity of the said main portion of the waveguide by means of a hole in the said main portion, and the said ring being capable of being opened and fitted around the malleus, without eroding it and being easily removable.

Furthermore according to the invention, this hook member may be a Causse prosthesis. Also according to the invention, the said extremity of the said main portion of the waveguide may be capable of being located close to the oval window or the round window or the promontory of the middle ear.

Advantageously according to the invention the said main portion of the said waveguide may be inserted beneath the tympanic ring by means of tympanotomy beneath the tympanic ring. Again according to the invention, the said main portion of the said waveguide can be inserted through the tympanum through myringotomy. Again according to the said invention, at least one further portion may be attached to the said main portion of the said waveguide through nesting. Further according to the invention, the said main portion of the said waveguide and the said at least one further portion may be telescopic. Preferably according to the invention the said waveguide may be made of semi-rigid material.

Advantageously according to the invention, at least one of the said portions of the said waveguide may comprise a Silverstein tube. Still in accordance with the invention, at least one of the said portions of the said waveguide may comprise a needle cannula. A reversed Silverstein tube may be nested in the needle cannula, with the tip of the prosthesis inserted into this.

Again according to the invention, the said prosthesis may comprise a unit which incorporates the said at least one microphone, the said amplifier, the said at least one audio transducer and the said power supply means; and in that the said waveguide comprises a second portion which can be attached to the said main portion and a third portion which can be attached to the said second portion and the said unit, the said third portion being capable of being closed off by means of a closure member when the said unit is separated from the said waveguide.

Furthermore according to the invention the said closure member may comprise a Silverstein plug and be therefore impenetrable to water. Advantageously according to the invention the said unit may be capable of being located beneath the auricle.

Again according to the invention, this prosthesis may comprise a first unit which incorporates the said at least one microphone on the said amplifier, the said first unit comprising a further waveguide capable of conveying surrounding sound waves to the said microphone, the said first unit being capable of being fitted beneath the skin below and behind the auricle of the prosthesis user, in such a way that the said further waveguide can emerge from the skin; and a second unit comprising the said at least one audio transducer, the said second unit being capable of being fitted within the auditory canal and connected to the said first unit through electrical wires; and in that the said power supply means are connected through electrical wires to the said first unit, which can be fitted behind the ear and can be secured to the auricle by means of an earclip; and the said waveguide comprising a second portion which can be attached to one extremity of the said main portion and the other extremity to the said second unit.

Again according to the invention, the said first unit and the said second unit may be connected by means of a disconnectable connector.

Further according to the invention, the said prosthesis may comprise signal processing means connected to the said microphone, capable of filtering audio frequencies. Preferably according to the invention, the said signal processing means are digital.

Advantageously according to the invention, the said prosthesis may comprise adjustment means connected to the said amplifier. Again according to the invention, the said adjustment means may comprise a trimmer.

Further according to the invention, the said power supply means may comprise a battery, preferably a rechargeable battery.

Another object of this invention is a procedure for implanting an acoustic prosthesis having direct action on the middle ear characterized in that it comprises the following stages:

(a) positioning the extremity of the first portion of a waveguide;

(b) inserting a needle cannula into the lower posterior portion of the canal through the skin and not the cartilage, the said needle cannula comprising a needle and a cannula capable of constituting the second portion of the waveguide;

(c) removing the needle from the needle cannula;

(d) inserting the cannula in the extremity of the first portion of the waveguide; and (e) connecting a unit to the said waveguide.

Again according to the invention, the said procedure may comprise the stage of performing a myringotomy or a tympanotomy of the tympanic ring of the middle ear before stage (a) for fitting the extremity of the said first portion of the said waveguide into the middle ear. Again according to the invention, the said procedure may also comprise the following stage: (f) fitting a third portion of the said waveguide connected to the said second portion and to the said unit.

DETAILED DESCRIPTION

Figure 1:
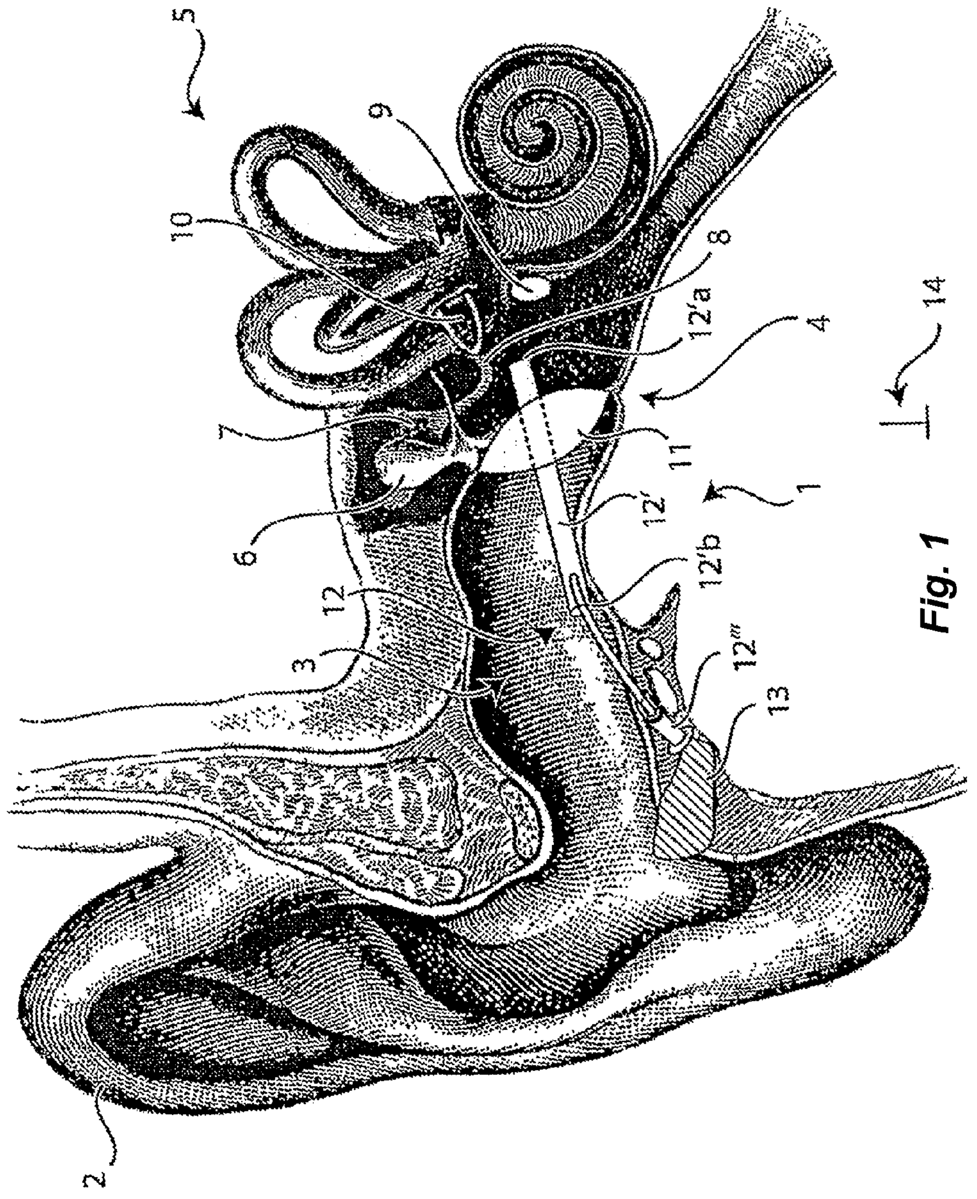
FIG. 1 shows a side view of the auditory canal in cross-section in which a first embodiment of the improved acoustic prosthesis acting directly on the middle ear according to this invention is fitted.
Figure 2:
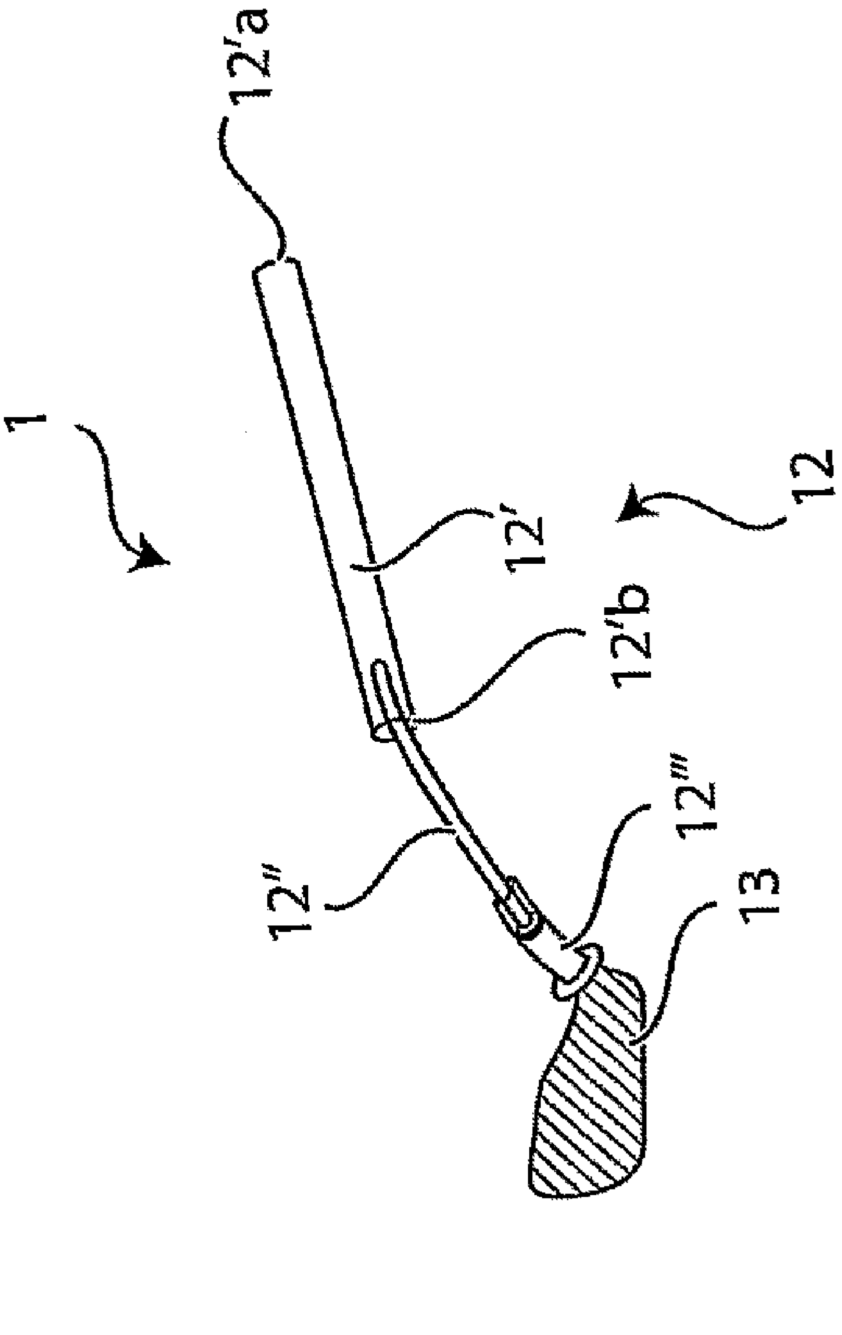
FIG. 2 shows a side view of the acoustic prosthesis according to FIG. 1.

With reference to FIGS. 1 and 2, these show a first embodiment of acoustic prosthesis 1. FIG. 1 in particular shows a cross-section of the human auditory apparatus in which may be seen the auricle 2, the auditory canal 3, the middle ear 4 and the inner ear 5. Within middle ear 4 may be seen the group of ossicles, malleus 6, incus 7 and stapes 8, the oval window 9 and the round window 10. As is known, malleus 6 is mechanically connected to tympanic membrane 11.

Acoustic prosthesis 1 comprises a waveguide 12 connected to a unit 13 incorporating a microphone which is able to capture surrounding sounds and an amplifier to amplify the sounds captured by the said microphone. An audio transducer is also present, together with a loudspeaker, connected to the said amplifier, the sound waves from which are delivered within middle ear 4 through waveguide 12. Acoustic prosthesis 1 may also comprise an internal digital signal processing unit which is in particular capable of filtering the audio signal. The amplifier, the microphone and any internal digital signal processing unit are electrically powered through a battery incorporated in unit 13.

Said waveguide 12 comprises a first portion 12' whose extremity 12'*a* can be fitted within middle ear 4, and a second portion 12". Extremity 12'*a* may be fitted within the middle ear through myringotomy, thus passing through tympanic membrane 11 (as in FIG. 1), or beneath the tympanic ring, through tympanotomy beneath the tympanic ring. Within middle ear 4 said extremity 12'*a* may preferably be positioned close to oval window 10 or round window 9. First portion 12' and second portion 12" can be connected together. In particular, in this embodiment said second portion 12" is nested into said first portion 12', in said first extremity 12'*a*. The other extremity of second portion 12" is in turn nested into a third portion of waveguide 12'" connected to unit 13. First portion 12' of waveguide 12 may take the form of a Silverstein tube.

Prosthesis 1 in question provides for only waveguide 12 to be fitted in auditory canal 3. This provides the following advantages:

- the electrical wires and cables are removed from auditory canal 3;
- auditory canal 3 remains substantially unobstructed. In fact first portion 12' of waveguide 12 of outer ear 3, that is the Silverstein tube, projects from beneath the skin of canal 3 by only 12 mm;
- unit 13 may be manipulated by the user extremely easily. Prosthetic 1 may be calibrated and in general may be adjusted by any audio technician once the ear specialist has implanted first portion 12" of waveguide 12;
- the materials used are all sterile, well known internationally, and commercially available;
- Larssen's phenomenon is absent due to the fact that the amplifier included in unit 13 is outside canal 3;
- if the user wishes to swim or undergo magnetic resonance or CAT, all that is necessary is to remove external unit 13 and close off the tube of third portion 12'" of waveguide 12 with a closure member 14 such as a Silverstein plug.

Figure 3:
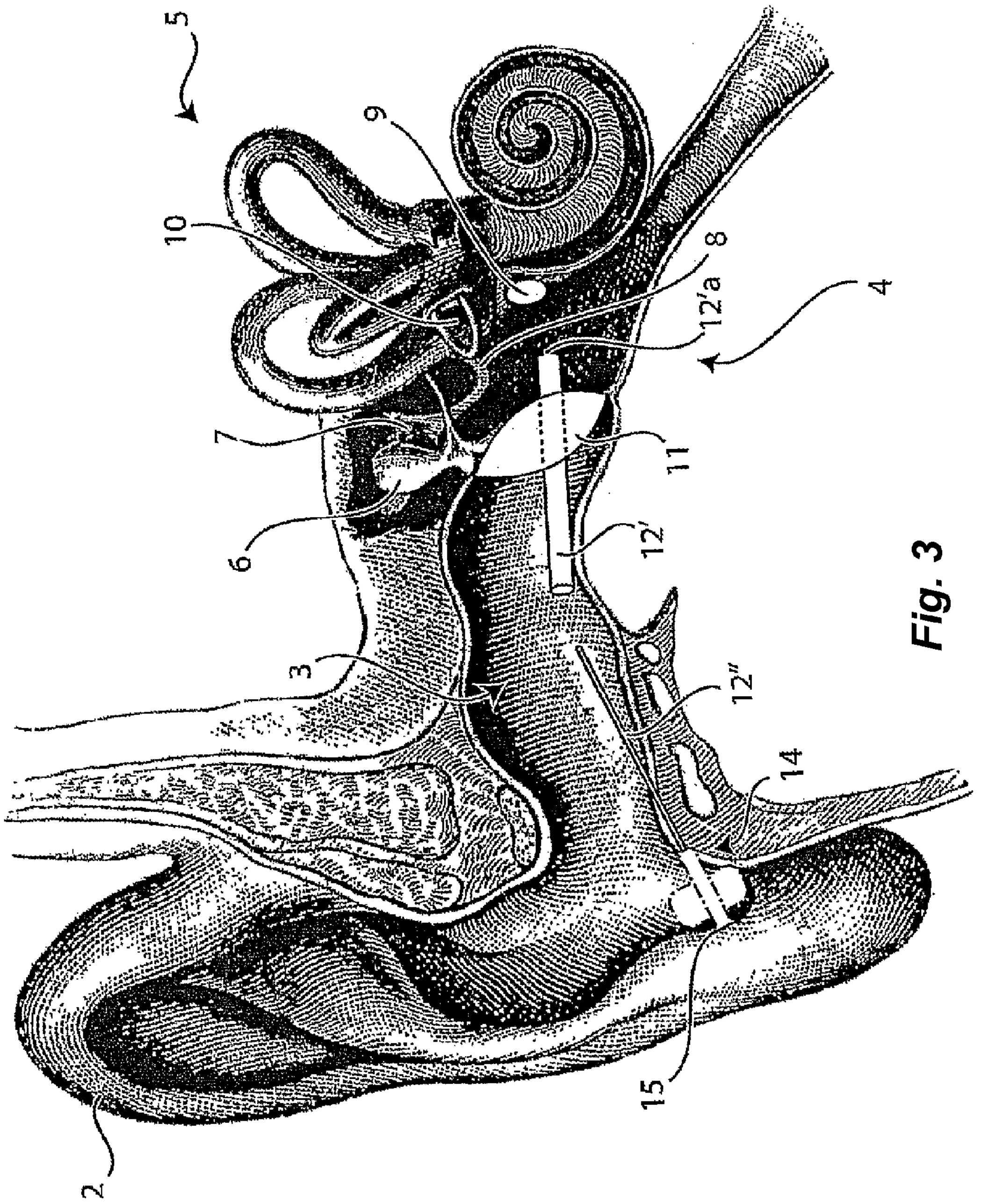
FIG. 3 shows a first stage in the procedure for fitting the acoustic prosthesis according to the invention.
Figure 4:
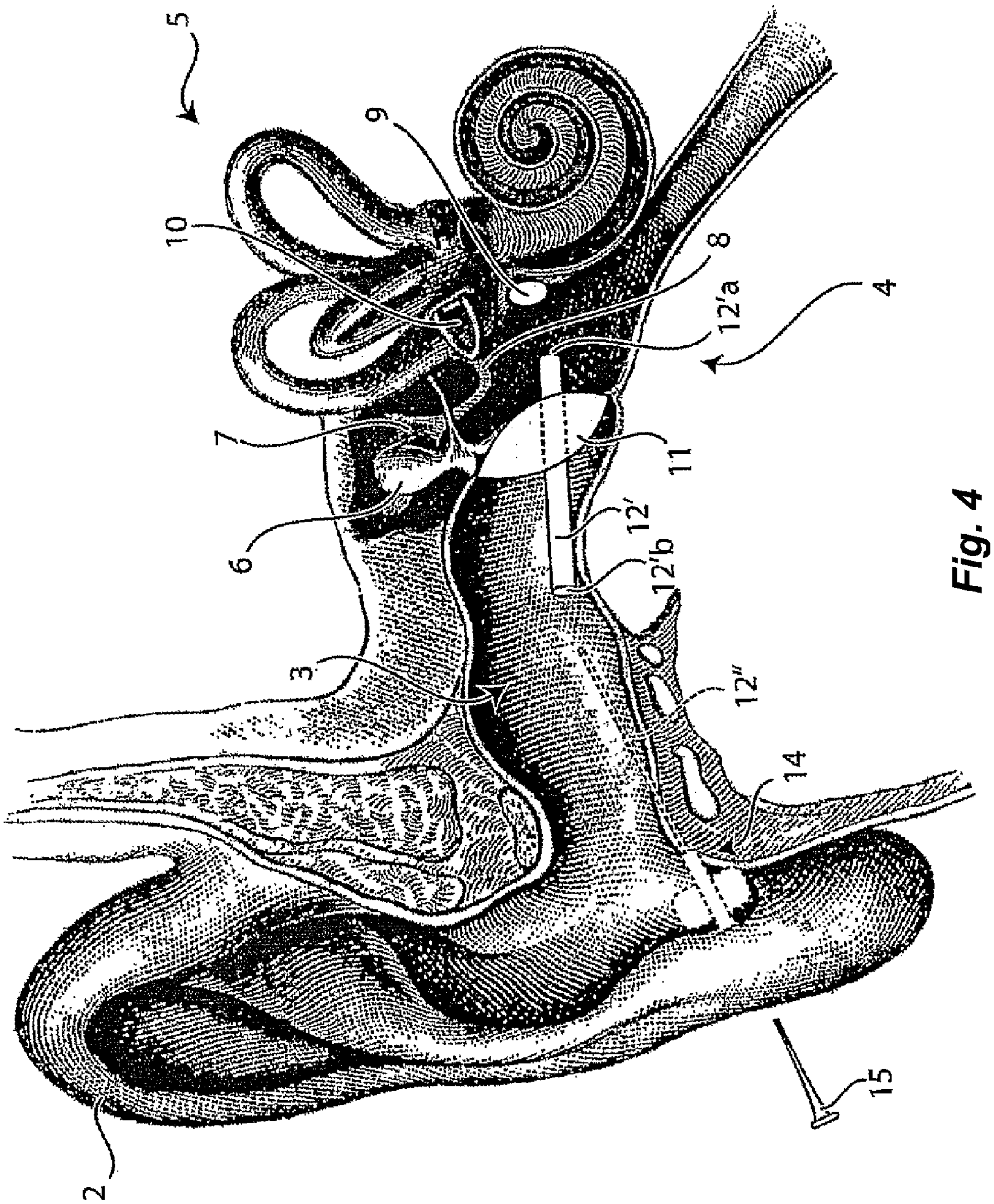
FIG. 4 shows a second stage in the procedure for fitting the acoustic prosthesis according to the invention.
Figure 5:
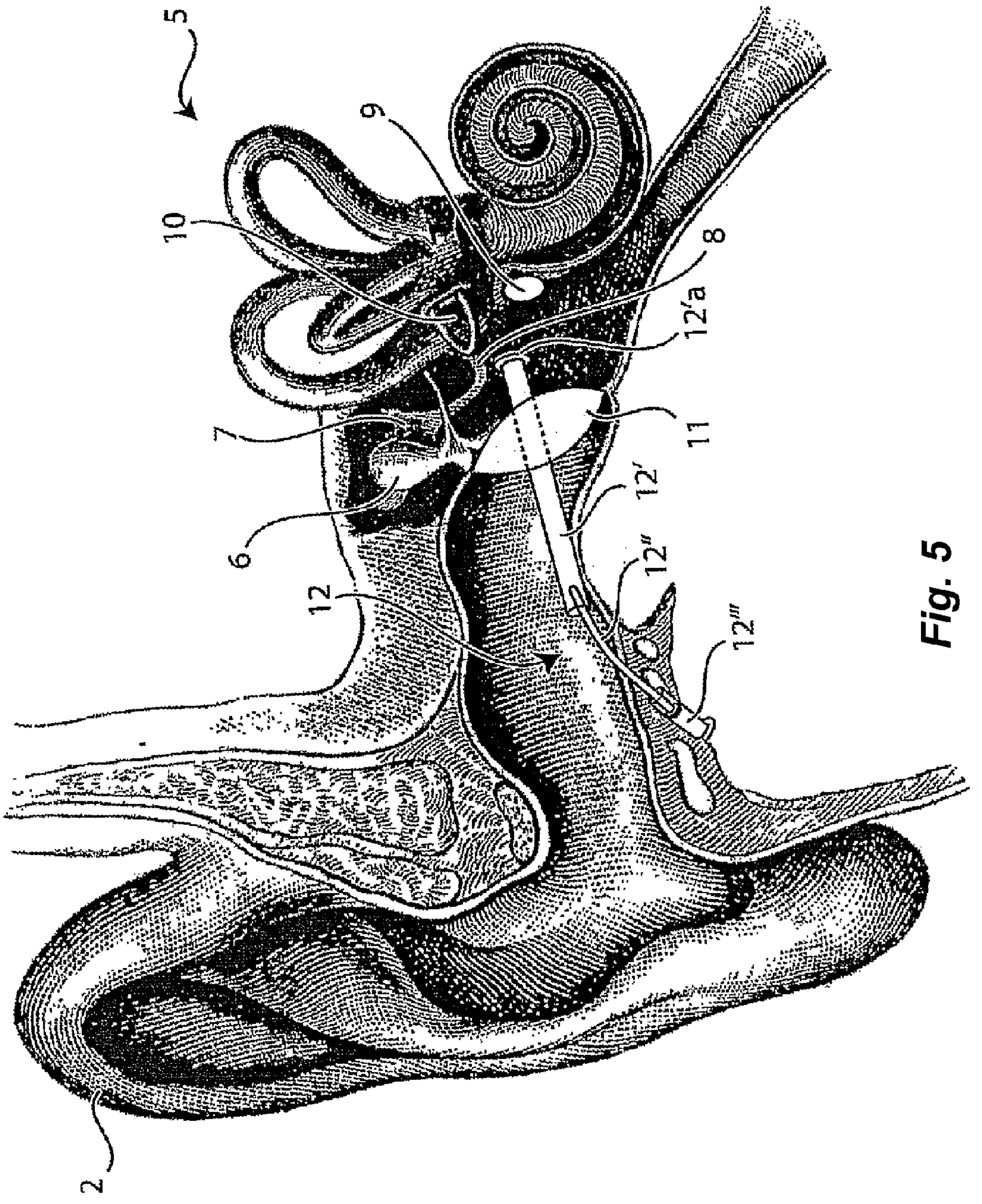
FIG. 5 shows a third stage in the procedure for fitting the acoustic prosthesis according to the invention.

With reference now to FIGS. 3-5 it will be seen how this acoustic prosthesis can easily be fitted. In particular the figures show the stages in fitting listed below:

- positioning extremity 12'*a* of first portion 12' of waveguide 12 (Silverstein tube) through myringotomy or tympanotomy of the tympanic ring of the middle ear (FIG. 3);
- insertion of a needle cannula 14, comprising a needle 15 and a cannula, which will then constitute the second portion 12" of waveguide 12, in the lower posterior portion of the canal through the skin and not the cartilage (FIG. 3);
- removal of needle 15 from needle cannula 14 (FIG. 4);
- insertion of cannula 12" (or second portion 12" of waveguide 12) into extremity 12'*b* of first portion 12' of waveguide 12;
- fitting a second Silverstein tube capable of forming third portion 12'" of waveguide 12;
- inserting said second portion 12" in said third portion 12'" of waveguide 12.

At this point waveguide 12 is fitted between middle ear 4 and auditory canal 3. All that is necessary is to connect unit 13 to said portion 12'" in order to complete the operation. As will be seen, second portion 12" of waveguide 12 is nothing more than an ordinary cannula or needle cannula, also known as a "vein-flow" cannula.

Figure 6:
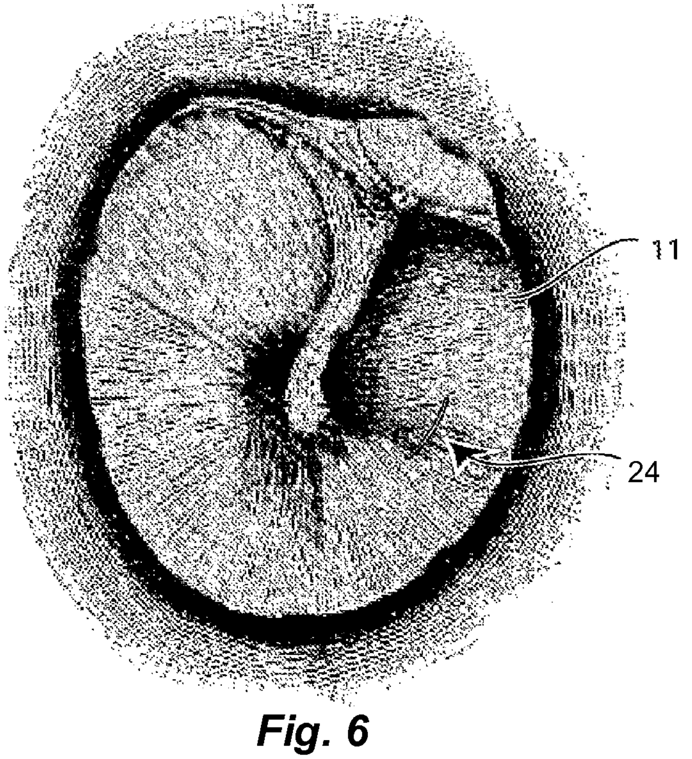
FIG. 6 shows a tympanic membrane in which a myringotomy has been performed to fit a waveguide.
Figure 7:
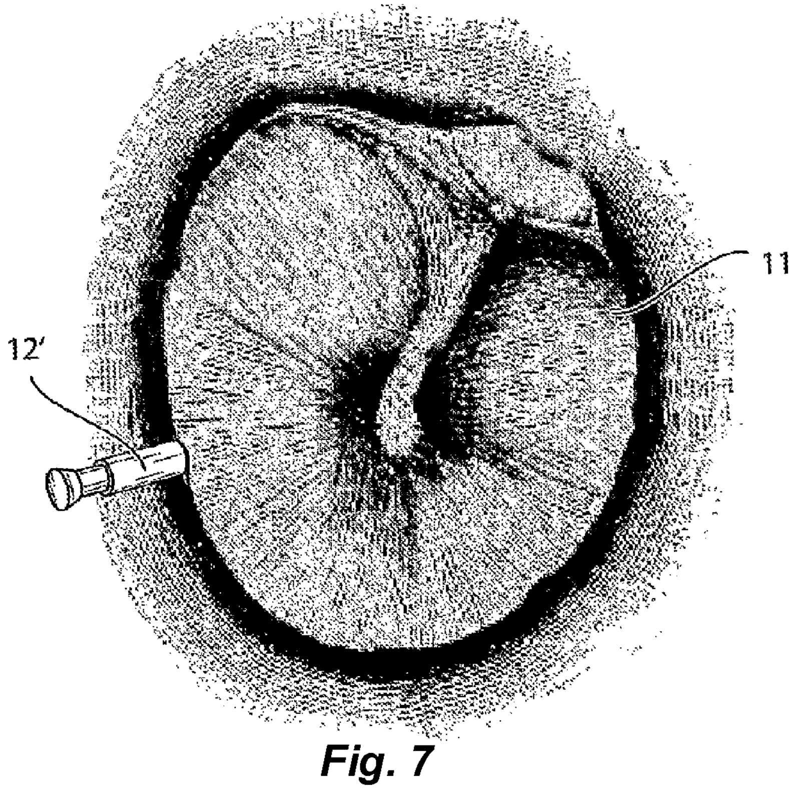
FIG. 7 shows a tympanic membrane in which a tympanotomy has been performed beneath the tympanic ring to fit a waveguide.

FIGS. 6 and 7 show the two main techniques through which first portion 12' of waveguide 12 can be inserted into the middle ear. In particular, FIG. 6 shows the incision line 24 along which the myringotomy or tympanotomy may be performed. The surrounding area is generally anesthetized using 80% saturated phenol. FIG. 7 on the other hand shows how the first portion 12' of waveguide 12 is inserted beneath the tympanic ring, through tympanotomy beneath the tympanic ring. Repositioned tympanum 11 and a Silverstein tube 12' will be seen in the figure.

Figure 8A:
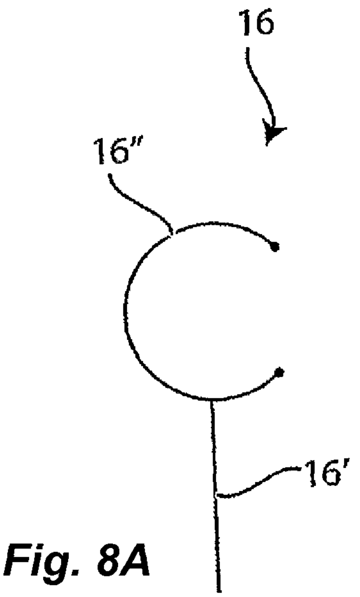
FIG. 8A shows an open Cousse prosthesis.
Figure 8B:
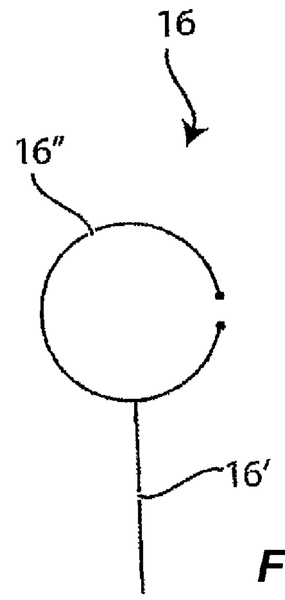
FIG. 8B shows a closed Cousse prosthesis.

As mentioned, a very important technical problem relating to prostheses having a direct action on the middle ear comprising a waveguide relates to securing extremity 12'*a* of first portion 12' of waveguide 12 in middle ear 4. With this object, in this invention a hook member 16 known as a Cousse prosthesis, which is wholly of plastics material and which may be seen in FIGS. 8A and 8B, is preferably used. Cousse prosthesis 16 has been known for a long time in ear nose and throat medicine, but is normally used by attaching it to the lenticular process of the incus through a stapedotomy with positioning within the otosclerosis. This prosthesis comprises a rigid longitudinal portion 16' and an openable ring 16". Because of the resilience properties of the material of which it is constituted, once it is open ring 16" requires a certain period of time to close again. This assists implantation of the prosthesis.

Figure 9:
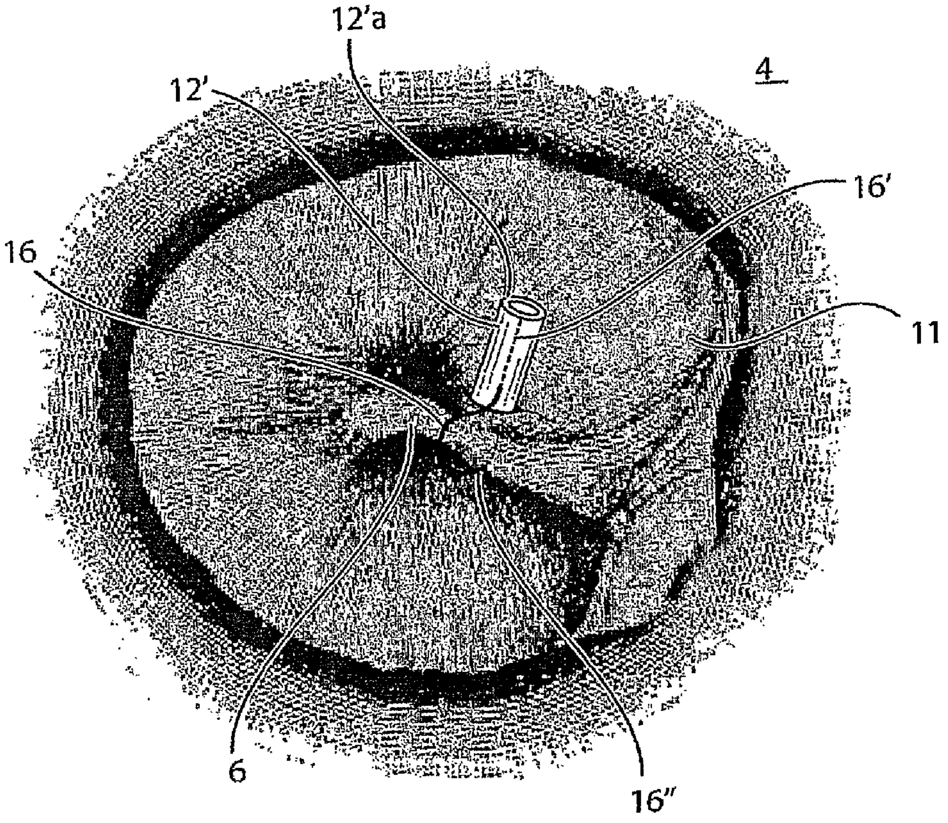
FIG. 9 shows a Cousse prosthesis fitted to a malleus.

As may be seen in FIG. 9, Cousse prosthesis 16 is attached to extremity 12'*a* of portion 12' by "passing" said portion 12' through rigid longitudinal portion 16'. Subsequently ring 16" may be opened and placed around malleus 6. In this way waveguide 12 is securely attached within middle ear 4. In addition to this, as said Cousse prosthesis 16 is made of plastics material the user may for example undergo instrument examinations such as cranial CAT or magnetic resonance without having to remove all acoustic protection 1, but only external electronic unit 13, as mentioned.

Figure 10:
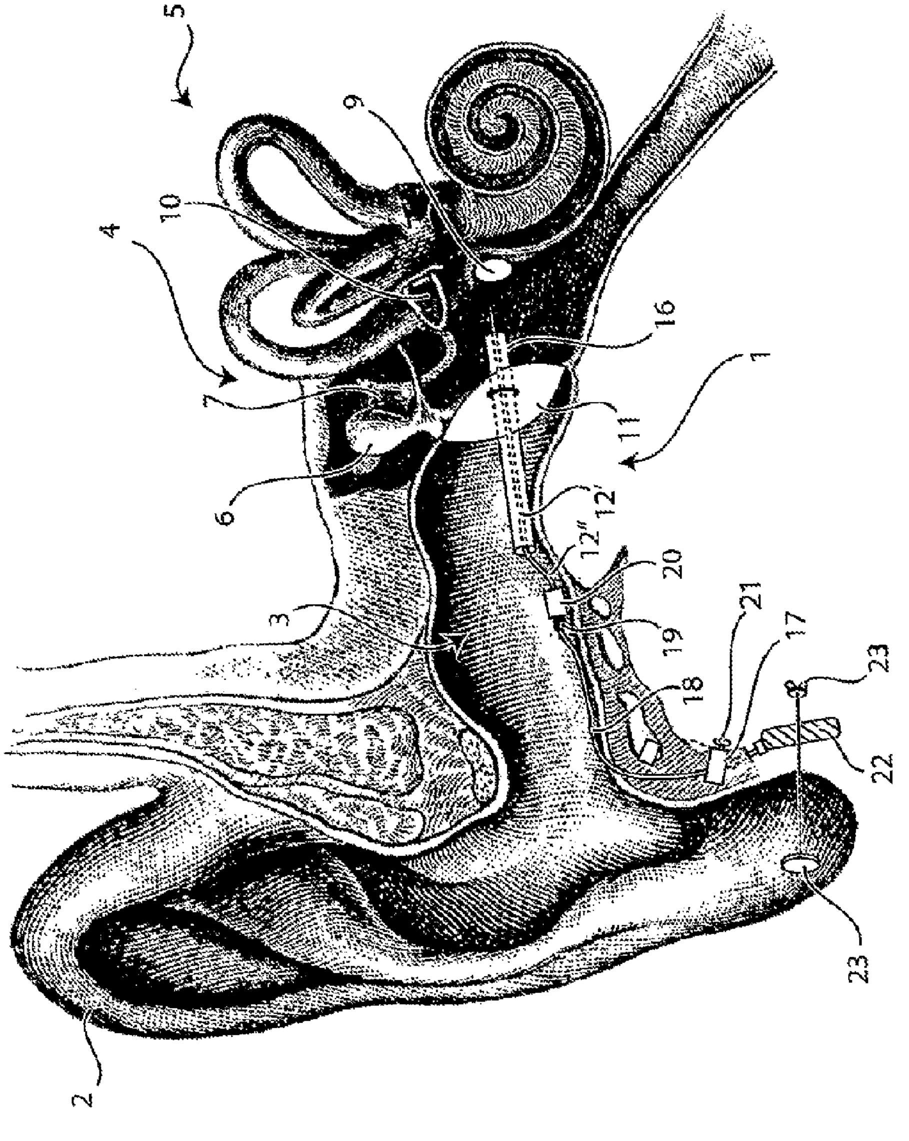
FIG. 10 shows a side view of the auditory canal in cross-section in which a second embodiment of the improved acoustic prosthesis acting directly on the middle ear according to this invention has been fitted.

FIG. 10 illustrates a second embodiment of an acoustic prosthesis 1 implanted according to this invention. Waveguide 12 comprising a first and second portion 12', 12" will be seen. Extremity 12'*a* of said first portion 12' is inserted into middle ear 4 through tympanum 11 by myringotomy. Acoustic prosthesis 1 comprises a first and a second unit, 17 and 20. Second portion 12" is connected to said second unit 20 containing a transducer, which is in turn connected to an electrical wire 18 and a removable connector 19 to said first unit 17 which incorporates an amplifier and a microphone. As will be seen, first unit 17 can be fitted beneath the skin. Sound waves from the amplifier reach the microphone and the amplifier through an entry waveguide 21. Finally said first unit 17 is powered by a battery 22 which can be placed behind the ear and can be attached thereto through an earclip 23.

Acoustic prosthesis 1 according to this embodiment is very discrete. Because of the fact that all the components are leak tight, all that is necessary is to close off entry waveguide 21 through closure member 14 (see FIG. 1). The user can therefore immerse himself in water without removing any part of the prosthesis. In any event acoustic prosthesis 1 is easy to remove because connector 19 is also present.

On the basis of the above description it will be seen that the fundamental feature of this invention is that it leaves the auditory canal substantially unobstructed, not adversely affecting the sound, and allows the waveguide to be efficiently anchored.

Although various exemplary embodiments of the invention have been disclosed, it should be apparent to those skilled in the art that various changes and modifications can be made which will achieve some of the advantages of the invention without departing from the true scope of the invention.

What is claimed is:

1. A middle ear prosthesis device comprising:

an outer ear unit including:

i. a sensing microphone for converting an acoustic audio signal into a corresponding electrical audio signal;

ii. a sensing amplifier for amplifying the electrical audio signal; and iii. an audio transducer for converting the amplified electrical audio signal into a corresponding amplified acoustic audio signal; and an acoustic waveguide having a plurality of tubular portions connected together in series for conducting the amplified acoustic audio signal from the audio transducer to the middle ear and including:

i. a main tubular portion having an outer end adapted for placement in the outer ear canal and an inner end adapted for placement in the middle ear, and ii. an extension portion having an outer end disconnectably fitted to the audio transducer and an inner end disconnectably fitted to the outer end of the main tubular portion.

2. A device according to claim 1, further comprising:

a hook element having a rigid longitudinal portion with:

i. a first end coupled to the inner end of the main tubular portion of the acoustic waveguide, and ii. a second end having a ring adapted for positioning about the malleus in the middle ear.

3. A device according to claim 1, wherein the main tubular portion of the acoustic waveguide is adapted for insertion through the tympani by myringotomy.

4. A device according to claim 1, wherein the outer end of the extension portion of the acoustic waveguide includes a needle cannula for receiving a needle.

* * * * *